United States Patent [19]

Arhancet

[11] Patent Number: 6,024,894
[45] Date of Patent: Feb. 15, 2000

[54] COMPOSITIONS AND METHODS FOR INHIBITING VINYL AROMATIC MONOMER POLYMERIZATION

[75] Inventor: Graciela B. Arhancet, Katy, Tex.

[73] Assignee: BetzDearborn Inc., Trevose, Pa.

[21] Appl. No.: 09/047,551

[22] Filed: Mar. 25, 1998

[51] Int. Cl.$^7$ .......................... C09K 15/08; C09K 15/16; C07C 7/20; C07C 7/148
[52] U.S. Cl. .............................. 252/404; 252/405; 585/4; 585/5; 585/832
[58] Field of Search .................................... 252/401, 404; 585/4, 5, 832

[56] References Cited

U.S. PATENT DOCUMENTS

| | | | |
|---|---|---|---|
| 2,965,685 | 12/1960 | Campbell | 260/666.5 |
| 3,674,651 | 7/1972 | Otsuki et al. | 203/8 |
| 3,733,326 | 5/1973 | Murayama | 260/290 |
| 3,747,988 | 7/1973 | Bailey | 203/8 |
| 4,003,800 | 1/1977 | Bacha et al. | 203/9 |
| 4,040,911 | 8/1977 | Bacha et al. | 203/9 |
| 4,105,506 | 8/1978 | Watson | 203/9 |
| 4,237,326 | 12/1980 | Fuga et al. | 585/4 |
| 4,376,678 | 3/1983 | Partos | 203/9 |
| 4,409,408 | 10/1983 | Miller | 585/4 |
| 4,434,307 | 2/1984 | Miller | 585/4 |
| 4,466,905 | 8/1984 | Butler et al. | 252/403 |
| 4,670,131 | 6/1987 | Ferrell | 208/48 AA |
| 4,720,566 | 1/1988 | Martin | 558/306 |
| 4,774,374 | 9/1988 | Abruscato et al. | 585/24 |
| 4,885,413 | 12/1989 | Campbell et al. | 570/104 |
| 4,956,020 | 9/1990 | Nakajima | 134/22.19 |
| 5,254,760 | 10/1993 | Winter et al. | 585/5 |
| 5,282,957 | 2/1994 | Wright et al. | 208/48 AA |
| 5,396,004 | 3/1995 | Arhancet | 585/5 |
| 5,426,257 | 6/1995 | Arhancet | 585/5 |
| 5,446,220 | 8/1995 | Arhancet | 585/5 |
| 5,489,718 | 2/1996 | Arhancet | 585/5 |
| 5,489,720 | 2/1996 | Arhancet | 585/5 |
| 5,510,547 | 4/1996 | Arhancet | 585/5 |
| 5,540,861 | 7/1996 | Grossi et al. | 252/404 |
| 5,545,782 | 8/1996 | Winter et al. | 585/5 |
| 5,545,786 | 8/1996 | Winter et al. | 585/435 |
| 5,562,863 | 10/1996 | Arhancet | 252/404 |
| 5,583,247 | 12/1996 | Nesvadba et al. | 560/2 |
| 5,616,774 | 4/1997 | Evans et al. | 560/4 |
| 5,627,248 | 5/1997 | Koster et al. | 526/217 |

FOREIGN PATENT DOCUMENTS

| | | |
|---|---|---|
| 163428 | 11/1971 | Czechoslovakia . |
| 240997A | 4/1986 | European Pat. Off. . |

*Primary Examiner*—D. Gabrielle Brouillette
*Assistant Examiner*—LaToya I Cross
*Attorney, Agent, or Firm*—Greenblum & Bernstein, P.L.C.

[57] ABSTRACT

Synergistic composition and method of use are disclosed. The compositions comprise a quinone methide derivative and a hydroxylamine compound. These compositions demonstrate synergism at inhibiting the polymerization of a vinyl aromatic monomer. Preferably the quinone methide derivative is 2,6-di-tert-butyl-4-benzylidene-cyclo-2,5-dienone and the hydroxylamine compound is N,N-bis (hydroxypropyl)hydroxylamine.

20 Claims, No Drawings

COMPOSITIONS AND METHODS FOR INHIBITING VINYL AROMATIC MONOMER POLYMERIZATION

FIELD OF THE INVENTION

The present invention pertains to compositions for use in inhibiting vinyl aromatic monomer polymerization.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, which is typically excluded from styrene distillation, will also promote polymerization of the monomer.

This polymerization results not only in loss of desired monomer end-product, but also in the uses of production efficiency caused by polymer formation and/or agglomeration of polymer on process equipment. Thermal polymerization, which typically occurs during distillation, of styrene monomer results in the formation of normal (i.e., linear) polymer. This resulting polystyrene polymer is characterized by its glassy and transparent appearance and its solubility in the styrene monomer and many organic solvents.

The compounds generally used commercially to inhibit polymerization of vinyl aromatic monomers are of the dinitrophenol family. For example, U.S. Pat. No. 4,105,506, Watson et al. teaches the use of 2,6-dinitro-p-cresol as a polymerization inhibitor for vinyl aromatic compounds. U.S. Pat. No. 4,466,905, Butler et al. teaches that a combination of 2,6-di-nitro-p-cresol and p-phenylenediamine will inhibit polymerization in a distillation column when oxygen is present. U.S. Pat. No. 4,774,374, Abruscato et al. teaches compositions for inhibiting the polymerization of vinyl aromatic compounds. The composition is an oxygenated product of the reaction of N-aryl-N'-alkyl-p-phenylenediamine with oxygen. U.S. Pat. Nos. 5,426,257 and 5,489,718, Arhancet, teach methods and compositions for inhibiting the polymerization of vinyl aromatic monomers comprising an oxime compound and a hydroxylamine compound and/or a phenylenediamine.

The use of hydroxylamine compounds for preventing polymerization of vinyl aromatic compounds is disclosed in U.S. Pat. No. 2,965,685, Campbell. Their use in combination with phenylenediamines is disclosed in U.S. Pat. Nos. 5,396,004 and 5,510,547, Arhancet et al.

U.S. Pat. Nos. 4,003,800 and 4,040,911, Bacha et al., teach methods for inhibiting the polymerization of styrene utilizing a quinone alkide compound without or with a hindered phenol compound, respectively. Preferably, the quinone alkide is a methide such as 2,6-di-t-butyl-4-methenyl quinone methide.

U.S. Pat. No. 5,616,774, Evans et al., discloses processes and compositions for inhibiting the polymerization of vinyl aromatic monomers using a 7-aryl quinone methide. U.S. Pat. No. 5,583,247, Nesvadba et al., teaches inhibiting the polymerization of ethylenically unsaturated monomers with a 7-substituted quinone methide.

None of these references has taught or suggested employing a hydroxylamine compound and a quinone methide derivative together to inhibit the polymerization of a vinyl aromatic monomer.

DETAILED DESCRIPTION OF THE INVENTION

Compositions comprising a quinone methide derivative and a hydroxylamine are provided. These compositions have utility in vinyl aromatic monomers for inhibiting the unwanted polymerization therein.

The quinone methide derivatives generally have the formula:

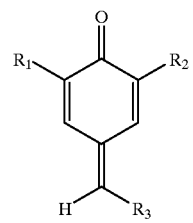

wherein:

$R_1$ and $R_2$ are independently H, $C_4$ to $C_{18}$ alkyl; $C_5$ to $C_{12}$ cycloalkyl; or $C_7$ to $C_{15}$ phenylalkyl.

Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred.

$R_3$ is preferably aryl, or aryl substituted with $C_1$ to $C_6$ alkyl, alkoxy, hydroxy, nitro, amino, carboxy, or mixtures thereof.

Means for preparing these compounds may be found in U.S. Pat. No. 4,032,547, the contents of which are wholly incorporated by reference to herein.

Preferably, the quinone methide derivative is 2,6-di-tert-butyl-4-benzylidene-cyclo-2,5-dienone.

The hydroxylamine compounds useful in the present invention generally have the formula

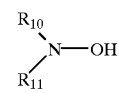

wherein $R_{10}$ and $R_{11}$ are the same or different and are hydrogen, alkyl, aryl, alkaryl, aralkyl, or hydroxyalkyl groups and preferably have about three to about twenty carbon atoms. The preferred hydroxylamine compound is N,N-bis(hydroxypropyl) hydroxylamine.

The compositions of the present invention are effective at inhibiting polymerization of vinyl aromatic monomers under processing conditions. These processing conditions include but are not limited to preparation, purification, distillation and vacuum distillation processes.

Styrene, for example, is typically processed at temperatures between 95° and 125° C. The compositions of the present invention are effective at inhibiting the polymerization of styrene over this range of temperatures.

The vinyl aromatic monomers that are treated by the compositions of the present invention include but are not limited to styrene, bromostyrene, divinylbenzene, and α-methylstyrene. The compositions of the present invention are particularly efficacious at inhibiting the polymerization of styrene monomer.

The total amount of quinone methide derivative and hydroxylamine compound used in the methods of the present invention is that amount which is sufficient to inhibit polymerization of vinyl aromatic monomers. This amount will vary according to the conditions under which the vinyl aromatic monomer is being processed, contaminants in the system and the temperature of the system. At higher processing temperatures and higher monomer contamination, larger amounts of the inhibiting composition are required.

For purposes of the present invention, the term "effective inhibiting amount" is that amount which is effective at inhibiting vinyl aromatic monomer polymerization. Preferably, this amount ranges from about 1 part to about 10,000 parts of quinone methide derivative and hydroxylamine compound per 1 million parts of monomer. Most preferably, this amount will range from about 1 part total to about 1000 parts per million parts monomer.

Accordingly, it is possible to produce a more effective vinyl aromatic monomer polymerization inhibiting treatment than is obtained by the use of either compound by itself when measured at comparable treatment levels. This synergism or enhanced activity between components allows for the concentration of each of the components to be lowered and the total quantity of polymerization inhibitor required, particularly at higher temperatures, may be lowered while achieving a commensurate level of polymerization inhibition.

As such, the weight ratio of quinone methide derivative to hydroxylamine compound will generally range from about 9:1 to about 1:9 with a weight ratio of about 2:3 to about 1:1 preferred. Most preferred is a weight ratio of about 1:1.

The compositions of the present invention can be introduced into the vinyl aromatic monomer by any conventional method at any point of the processing system, either as separate and individual ingredients or as a combination of ingredients.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer to be treated may be employed. It is often desirable to dissolve the inhibitors in the monomer to which the inhibitor is being added to avoid introducing additional impurities in the monomer.

In order to more clearly illustrate the invention, the data set forth below were developed. The following examples are included as being illustrations of the invention and should not be construed as limiting the scope thereof.

EXAMPLES

Uninhibited styrene (5 mL) was placed in a test tube and the appropriate amount of treatment was added. The tube was capped with a rubber septum and argon was bubbled through the liquid at 10 mL/min. for 3 minutes. The tubes were then placed in an oil bath heated to 110° C. for 2 hours. The amount of polystyrene formed was determined by methanol precipitation. The results of this testing are presented in Table I.

TABLE I

| | Uninhibited Styrene Test 110° C. | |
|---|---|---|
| Treatment | Dose (ppm) | % Polymer |
| Blank | — | 6.07 |
| A | 400 | 0.46 |
| B | 400 | 1.36 |
| A/B | 200/200 | 0.03 |

Treatment A is 2,6-di-tert-butyl-4-benzylidene-cyclo-2,5-dienone.
Treatment B is N,N-bis(hydroxypropyl)hydroxylamine (HPHA).

The results presented in Table I demonstrate that the inventive composition is more effective than either ingredient by itself. Synergism is demonstrated at a 1 to 1 weight/weight ratio.

Further testing was performed using a known inhibitor compound, dinitro ortho cresol (DNOC) as a comparative inhibitor. 100 mL of uninhibited styrene was placed in a 250 mL three-necked flask fitted with a bubbler, a septa, and a condenser. The appropriate treatment was added and argon was bubbled through the solution at 10 ml/min. for 10 minutes. While argon sparging continued, the flask was immersed in an oil bath heated to 120° C. 5.0 mL samples were taken every 30 minutes and the amount of polymer formed was determined by methanol precipitation. Results of this testing are presented in Table II.

TABLE II

| | Uninhibited Styrene Test 120° C. | | | |
|---|---|---|---|---|
| Time | Percent Polymer | | | |
| (Min.) | Run 1 | Run 2 | Run 3 | Run 4 |
| 0 | 0 | 0 | 0 | 0 |
| 30 | 0.02 | 0.09 | 0.03 | 0.03 |
| 60 | 0.10 | 0.22 | 0.12 | 0.11 |
| 90 | 0.27 | 0.49 | 0.22 | 0.23 |
| 120 | 0.50 | 0.96 | 0.30 | 0.33 |
| 150 | 0.72 | 1.47 | 0.45 | 0.43 |
| 180 | 0.95 | 2.10 | 0.59 | 0.53 |
| 210 | 1.17 | 3.13 | 0.75 | 0.64 |
| 240 | 1.39 | 4.31 | 1.00 | 0.72 |
| 270 | 1.66 | 5.79 | 1.30 | 0.81 |
| 300 | 2.16 | — | 1.56 | 0.88 |

Run 1 is DNOC
Run 2 is 2,6-di-tert-butyl-4-benzylidene-cyclo-2,5-dienone
Run 3 is 300 ppm of 2,6-di-tert-butyl-4-benzylidene-cyclo-2,5-dienone and 300 ppm of HPHA
Run 4 is 200 ppm of 2,6-di-tert-butyl-4-benzylidene-cyclo-2,5-dienone and 300 ppm of HPHA This testing demonstrates that the inventive composition at 1:1 and 2:3 ratios was more effective than the quinone methide derivative and DNOC by themselves.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl aromatic monomers comprising adding to said monomers an effective polymerization inhibiting amount of a composition comprising (A) a quinone methide derivative having the formula

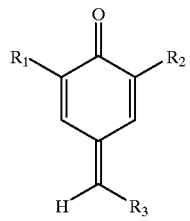

wherein:
R$_1$ and R$_2$ are independently C$_4$ to C$_{18}$alkyl; C$_5$ to C$_{12}$ cycloalkyl; or C$_7$ to C$_{15}$ phenylalkyl, and $R_3$ is aryl, or aryl substituted with $C_1$ to $C_6$ alkyl, alkoxy, hydroxy, nitro, amino, carboxy, or mixtures thereof; and (B) a hydroxylamine compound having the formula

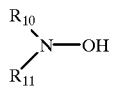

wherein $R_{10}$ and $R_{11}$ are the same or different and are hydrogen, alkyl, aryl, alkaryl, aralkyl, or hydroxyalkyl groups and preferably have about three to about twenty carbon atoms wherein the weight ratio of (A) to (B) is about 9:1 to about 1:9.

2. The method as claimed in claim 1 wherein said quinone methide derivative is 2,6-di-tert-butyl-4-benzylidene-cyclo-2,5-dienone.

3. The method as claimed in claim 1 wherein said hydroxylamine compound is a hydroxyalkylhydroxylamine.

4. The method as claimed in claim 3 wherein said hydroxylamine compound is N,N-bis(hydroxypropyl) hydroxylamine.

5. The method as claimed in claim 1 wherein said vinyl aromatic monomer is selected from the group consisting of styrene, bromostyrene, divinylbenzene and α-methylstyrene.

6. The method as claimed in claim 1 wherein the temperature of polymerization of said vinyl aromatic monomer ranges from about 95° to about 125° C.

7. The method as claimed in claim 1 wherein said composition is added to said monomer in an amount ranging from about 1 to about 10,000 parts per million parts of said monomer.

8. The method as claimed in claim 1 wherein the weight ratio of (A) to (B) is about 9:1 to about 2:3 to about 1:1.

9. The method as claimed in claim 1 wherein the weight ratio of (A) to (B) is about 1:1.

10. The method as claimed in claim 1 wherein (A) is 2,6-di-tert-butyl-4-benzylidene-cyclo-2,5-dienone and (B) is N,N-bis(hydroxypropyl)hydroxylamine.

11. A composition comprising (A) a quinone methide derivative having the formula:

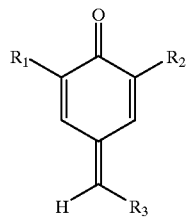

wherein:
$R_1$ and $R_2$ are independently $C_4$ to $C_{18}$ alkyl; $C_5$ to $C_{12}$ cycloalkyl; or $C_7$ to $C_{15}$ phenylalkyl, and
$R_3$ is aryl, or aryl substituted with $C_1$ to $C_6$ alkyl, alkoxy, hydroxy, nitro, amino, carboxy, or mixtures thereof, and (B) a hydroxylamine compound having the formula

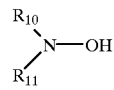

wherein $R_{10}$ and $R_{11}$ are the same or different and are hydrogen, alkyl, aryl, alkaryl, aralkyl, or hydroxyalkyl groups and preferably have about three to about twenty carbon atoms wherein the weight ratio of (A) to (B) is about 9:1 to about 1:9.

12. The composition as claimed in claim 11 wherein said quinone methide derivative is 2,6-di-tert-butyl-4-benzylidene-cyclo-2,5-dienone.

13. The composition as claimed in claim 11 wherein said hydroxylamine compound is a hydroxyalkyl hydroxylamine.

14. The composition as claimed in claim 13 wherein said hydroxylamine compound is N,N-bis(hydroxypropyl) hydroxylamine.

15. The composition as claimed in claim 11 wherein the weight ratio of (A) to (B) is about 2:3 to about 1:1.

16. The composition as claimed in claim 11 wherein the weight ratio of (A) to (B) is about 1:1.

17. The composition as claimed in claim 11 wherein (A) is 2,6-di-tert-butyl-4-benzylidene-cyclo-2,5-dienone and (B) is N,N-bis(hydroxypropyl)hydroxylamine.

18. The composition as claimed in claim 17 wherein the weight ratio of (A) to (B) is about 2:3 to about 1:1.

19. The composition as claimed in claim 11 wherein there is synergism between (A) and (B) as a vinyl aromatic monomer polymerization inhibitor.

20. The composition as claimed in claim 11 further comprising styrene.

* * * * *